United States Patent

Takasu et al.

Patent Number: 5,053,222
Date of Patent: Oct. 1, 1991

[54] HAIR COSMETIC COMPOSITION

[75] Inventors: Emiko Takasu, Tokyo; Kazumi Ogata, Osaka; Yoshihisa Sato, Yokohama, all of Japan

[73] Assignees: Shiseido Company Ltd., Tokyo; Senju Pharmaceutical Co., Ltd., Osaka, both of Japan

[21] Appl. No.: 362,543

[22] Filed: Jun. 7, 1989

[51] Int. Cl.$^5$ .............................. A61K 7/075
[52] U.S. Cl. ...................... 424/7; 514/852; 514/458; 514/148
[58] Field of Search .................. 424/70; 514/852, 458, 514/100, 148

[56] References Cited

U.S. PATENT DOCUMENTS 4,564,861  1/1986  Ogata .................... 549/220

FOREIGN PATENT DOCUMENTS 158090   10/1985  European Pat. Off. ............ 514/458
2301585   7/1974  Fed. Rep. of Germany .
51-73137   6/1976  Japan .
139114    6/1988  Japan .

Primary Examiner—Thurman K. Page
Assistant Examiner—Susan S. Rucker
Attorney, Agent, or Firm—Sprung Horn Kramer & Woods

[57] ABSTRACT

A hair cosmetic composition containing, as an active component, a diester of phosphoric acid with ascorbic acid and tocopherol, having the formula (I), and/or a salt thereof:

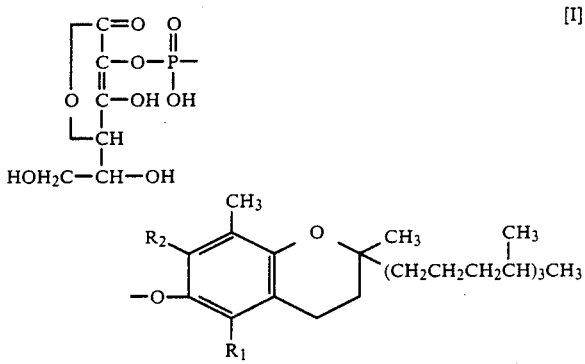

wherein $R_1$ represents H or $CH_3$ and $R_2$ represents H or $CH_3$.

2 Claims, No Drawings

HAIR COSMETIC COMPOSITION

BACKGROUND OF THE INVENTION

1. Field of the Invention

The present invention relates to a hair cosmetic composition especially a hair cosmetic composition for preventing dandruff and a loss of hair, which contains, as an active component, a diester of phosphoric acid with ascorbic acid and tocopherol, having the following general formula (1), and/or a salt thereof:

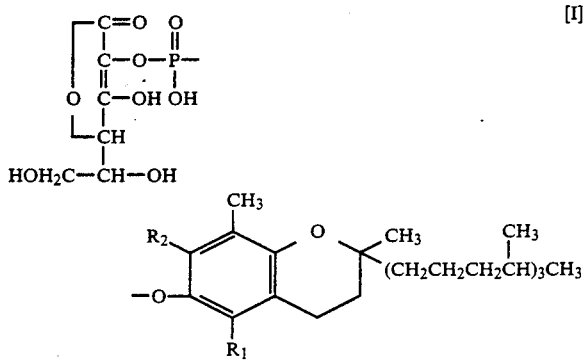

wherein $R_1$ represents H or $CH_3$ and $R_2$ represents H or $CH_3$

The diester of phosphoric acid with ascorbic acid and tocopherol according to the present invention has a structure in which two of three hydroxyl groups of phosphoric acid are esterified by one hydroxyl group each of ascorbic acid and tocopherol.

2. Description of the Related Art

In general, dandruff comprises exudates of sebaceous glands, exudates of sweat glands, and substances exfoliated and peeled from epidermal tissue layers, and usually dandruff is formed by an exacerbation of a secretion in sebaceous glands and the like. It is considered that, if the skin is infected with bacteria or yeasts, the generation of dandruff is greatly increased and a loss of hair occurs, and accordingly, hair cosmetics comprising an antibacterial agent or fungicide have been used as a hair cosmetic for preventing dandruff or a loss of hair. Some of these antibacterial agents and fungicides irritate the skin and are disadvantageous from the view point of the safety of a human body. Furthermore, it has been pointed out that if a cosmetic comprising an antibacterial agent or fungicide is used continuously day after day, a delicate balance among skin bacteria is destroyed and an unpreferable ecological condition is brought into existence. For example, zinc pyrithion (ZPT), considered to be most effective among conventional dandruff-preventing agents, falls under the category of an "antibacterial agent" and it is considered that an excessive use of this agent should be avoided.

Accordingly, there is an urgent need to prevent dandruff or a loss of hair without using an antibacterial agent or fungicide, and intensive research is underway into the development of safe substances having an effective dandruff-controlling action without an antibacterial or fungicidal action.

As substances exerting a dandruff-controlling effect not based on an antibacterial or fungicidal action, there have been reported an α-tocopherol/vitamin A acid ester (Japanese Unexamined Patent Publication No. 51-73137) and a vitamin E/nicontinic acid ester. (German Patent No. 2,301,585 and German Patent No. 2,301,660).

These conventional tocopherol esters, however, are not stable on the skin and do not have a long-term dandruff-control effect. Further, since the tocopherol esters are insoluble in water, they are defective in that oily precipitates are formed in certain forms of cosmetics. Furthermore, to incorporate the necessary amounts of these esters, large quantities of surface active agents must be used, and thus the use of these tocopherol esters becomes expensive.

SUMMARY OF THE INVENTION

Accordingly, the objects of the present invention are to eliminate the above-mentioned disadvantages of the prior art and to provide a hair cosmetic composition having an improved dandruff-preventing effect, safety, and stability.

Other objects and advantages of the present invention will be apparent from the following description.

In accordance with the present invention, there is provided a hair cosmetic composition comprising (i), as an active component, at least one component selected from the group consisting of diesters of phosphoric acids with ascorbic acid and tocopherol, represented by the following general formula (I) and salts thereof:

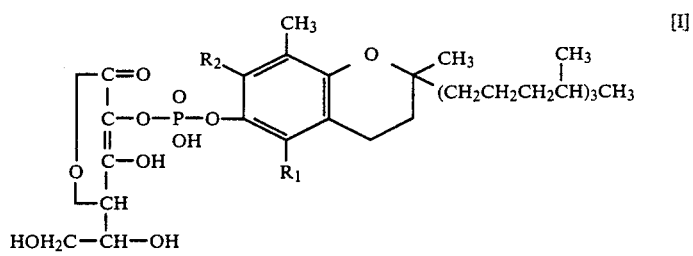

wherein $R_1$ represents H or $CH_3$ and $R_2$ represents H or $CH_3$; and (ii) a carrier.

DESCRIPTION OF THE PREFERRED EMBODIMENTS

The present inventors tested various tocopherol derivatives to determine their dandruff-preventing effects, with a view to overcoming the foregoing defects of the conventional tocopherol esters, and as a result, found that a diester of phosphoric acid with ascorbic acid and tocopherol and/or a salt thereof has a remarkable effect and an improved safety and stability. The present invention is based on this finding.

Any of α-, β-, γ- and δ-tocopherols can be used as the tocopherol constituting the diester of phosphoric acid with ascorbic acid and tocopherol, and the relationship between the type of the tocopherol and $R_1$ and $R_2$ in the above general formula is as described below.

| Type | $R_1$ | $R_2$ |
| --- | --- | --- |
| α | CH$_3$ | CH$_3$ |
| β | CH$_3$ | H |
| γ | H | CH$_3$ |
| δ | H | H |

The diester of phosphoric acid with ascorbic acid and tocopherol and its salt used in the present invention can be prepared, for example, by the following process disclosed in Japanese Unexamined Patent Publication No. 59-219295 (i.e., U.S. Pat. No. 4,564,686). More specifically, tocopherol is reacted with a halogenophosphorylating agent. This reaction proceeds rapidly in a non-reactive solvent in the presence of a deacidifying agent, and the obtained product is reacted with an ascorbic acid in which the hydroxyl groups in the 5- and 6-positions are protected by protecting groups. This reaction proceeds in a solvent such as tetrahydrofuran, in the presence of a deacidifying agent, and thus the protecting groups are eliminated, whereby the diester of phosphoric acid with ascorbic acid and tocopherol according to the present invention is prepared.

The phosphoric acid diester of the present invention can be used in the form of either a free acid or a salt. As the salt, there can be mentioned an organic amine salt and an inorganic salt. As the organic amine salt, there can be mentioned an aminomethylpropanol salt, an aminohydroxylmethylpropane-diol salt, an aminomethylpropane-diol salt, an isopropanolamine salt, a monoethanolamine salt, a diethanolamine salt, a triethanolamine salt, a morpholine salt, a glucosamine salt, and a diisopropanolamine salt, and as the inorganic salt, there can be mentioned a sodium salt, a potassium salt, a lithium salt, a calcium salt, and a magnesium salt. Of these salts, for example, the sodium salt and potassium salt are soluble in water but the calcium salt, for example, is insoluble in water. Therefore, an appropriate salt can be selected according to the intended object.

The phosphoric acid diester and its salt can be freely dissolved in water or an oil directly or after dissolving it in water, an alcohol or an aqueous solution of an alcohol, and therefore, the application range is broader than that of tocopherol or the like.

In the present invention, at least one member selected from the group consisting of diesters of phosphoric acid with ascorbic acid and tocopherol and salts thereof is used. The diester of phosphoric acid or its salt can be incorporated in an amount of 0.01 to 10% by weight (all of "%" given hereinafter are by weight), preferably 0.05 to 2%, based on the total amount of the hair cosmetic composition. If the amount is smaller than 0.01%, the dandruff-preventing effect is poor, and even if the amount is larger than 10%, a further increase of the effect cannot be expected.

By the hair cosmetic referred to in the present invention is meant a variety of cosmetics to be applied to the hair and skin of the head, for example, hair tonics, hair liquids, head skin milky lotions, hair creams, hair shampoos, and hair rinses.

Other hair-treating agents such as dandruff-preventing agents and loss of hair-preventing agents, and usual components, can be incorporated into the hair cosmetic composition of the present invention.

For example, as the other dandruff-preventing agent, there can be mentioned ZPT, TCC, hinokitiol, α-tocopherol/vitamin A acid ester, vitamin E/nicotinic acid ester, vitamin E/acetic acid ester, selenium sulfide, thioxolone, sulfur, salicylic acid, resorcinol, hexachlorophene, tetrachlorosalicylanilid, benzalconium chloride, and quaternary ammonium salts such as octadecyltrimethyl ammonium chloride and hexadecyldimethylbenzyl ammonium chloride. Further, any other forms of hair-treating agents can be used. As other ingredients to be incorporated in the hair cosmetic of the present invention, there can be mentioned inorganic powders such as talc, kaolin, sericite, white mica, gold mica, red mica, black mica, lithia mica, vermiculite, synthetic mica, magnesium carbonate, calcium silicate, aluminum silicate, barium silicate, barium sulfate, strontium silicate, metal tungstates, silica, zeolites, boron nitride, barium sulfate, calcined calcium sulfate (calcined gypsum), calcium phosphate, fluorine apatite, powdery ceramics and metal soaps (such as zinc myristate, calcium palmitate and aluminum stearate), organic powders such as polyamide resin powder (nylon powder), polyethylene powder, polymethyl methacrylate, polystyrene powder, styrene/acrylic acid copolymer resin powder, benzoguanamine resin powder, polytetrafluoroethylene powder and cellulose powder, inorganic white pigments such as titanium dioxide and zinc oxide, inorganic red pigments such as iron oxide (red iron oxide) and iron titanate, inorganic brown pigments such as γ-iron oxide, inorganic yellow pigments such as yellow iron oxide and ochre, inorganic black pigments such as black iron oxide, carbon black, low titanium oxide antinium oxynitride, inorganic violet pigments such as Mango Violet and Cobalt Violet, inorganic green pigments such as chromium oxide, chromium hydroxide, and cobalt titanate, inorganic blue pigments such as ultramarine and prussian blue, pearl pigments such as titanium oxide-coated mica, bismuth oxychloride, titanium oxide-coated bismuth oxychloride, titanium oxide-coated talc, colored titanium oxide-coated mica, and fish scale, metal powder pigments such as aluminum powder and copper powder, organic dyes and pigments such as Red 201, Red 202, Red 204, Red 205, Red 220, Red 226, Red 228, Red 405, Orange 203, Orange 204, Yellow 205, Yellow 401, and Blue 404, zirconium-, barium-, and aluminum-chelate organic pigments such as Red 3, Red 104, Red 106, Red 227, Red 230, Red 401, Red 505, Orange 205, Yellow 4, Yellow 5, Yellow 202, Yellow 203, Green 3, and Blue 1, natural colors such as chlorophyll, β-carotene, and calsamine, animal-and plant-derived oils such as avocado oil, camellia oil, academia nut oil, corn oil, olive oil, evening primrose oil, rape oil, yolk oil, sesame oil, persic oil, wheat germ oil, sasaqua oil, castor oil, hardened castor oil, linseed oil, safflower oil, sunflower oil, cotton seed oil, soybean oil, peanut oil, tea seed oil, nutmeg oil, rice bran oil, chinese tung oil, Japanese tung oil, jojoba oil, germ oil, sugar cane wax, cacao fat, coconut oil, hardened coconut oil, turtle oil, mink oil, squalene, squalane, orange raffinate, beef tallow, horse tallow, sheep tallow, pig tallow, beef cattle bone fat, beef cattle leg fat, hardened beef tallow, wood wax, bees wax, candelilla wax, cotton wax, carnauba wax, bayberry wax, insect wax, spermaceti, bran wax, kapok wax, lanolin, lanolin alcohol, hydrous lanolin, jojoba wax, shellac, POE lanolin alcohol acetate, POE cholesterol ether, lanolin fatty acid polyethylene, and POE hydrogenated lanolin alcohol ether, microorganism-derived oils such as oils produced by microorganisms belonging to the genus Mortierella, mineral-derived oils such as liquid paraffin, ozocerite, pristane, ceresine, vaseline and micro-crystalline wax, higher alcohols such as capryl alcohol, lauryl alcohol, cetyl alcohol, stearyl alcohol, arachidic alcohol, behenyl alcohol, oleyl alcohol, cetostearyl alchol, monostearyl glyceryl ether (patchouli oil), 2-decyltetradecanol, 2-hexyldecanol, 2-hexyldodecanol, 2-octyldodecanol, cholesterol, phytosterol and isostearyl alcohol, higher fatty acids such as caprylic acid, lauric acid, myristic acid, palmitic acid, stearic acid, behenic acid (behenine), 12-hyiroxystearic acid, undecylenic acid, lanoline fatty acid, isostearic acid, linoleic acid, oleic acid, ricinoleic acid, arachidic acid, arachidonic acid, and eicosapentaenoic acid, ester oils such as isopropyl myristate, cetyl octanoate, octyldodecyl myristate, isopropyl palmitate, butyl stearate, hexyl laurate, myristyl myristate, decyl oleate, hexyldecyl dimethyloctanoate, cetyl lactate, myristyl lactate, lanolin acetate, isostearyl stearate, isocetyl isostearate, cholesteryl 12-hydroxystearate, ethylene glycol di-2-ethylhexanoate, dipentaerythritol fatty acid esters, N-alkylglycol nonoisostearate, neopentyl glycol dicaprane, diisostearyl malate, glyceryl di-2-heptylundecanoate, trimethylol-propane tri-2-ethylhexanoate, trimethylol-propane triisostearate, pentaerythritol tetra-2-ethylhexanoate, glyceryl tri-2-ethylhexanoate trimethylol-propane triisostearate, cetyl 2-ethylhexanoate, 2-ethylhexyl palmitate, glyceryl trimyristate, glyceryl trioctanoate, glyceryl triisopalmitate, glyceryl tri-2-heptylundecanoate, methyl castor oil fatty acid ester, lanoline alcohol acetate, isopropyl lanoline fatty acid ester, oleyl oleate, glyceryl triacetate, 2-butylundecyl palmitate, diisobutyl adipate, 2-octyldecyl N-lauroyl-L-glutamate, di-2-heptylundecyl adipate, ethyl laurate, di-2-ethylhexyl sebacate, 2-hexyldecyl myristate, 2-hexyldec, 1-palmitate, diisopropyl sebacate and 2-ethylhexyl succinate PABA type ultraviolet absorbants such as p-aminobensoic acid (hereinafter referred to as "PABA "), PABA butyl ester, PABA glyceryl ester, N,N-dipropoxy PABA ethyl ester, N,N-diethoxy PABA ethyl ester, N,N-dimethyl PABA ethyl ester, N,N-dimethyl PABA amyl ester and N,N-dimethyl PABA iso-octyl ester, salicylic acid type ultraviolet absorbers such as amyl salicylate, menthyl salicylate, homomentyl salicylate, octyl salicylate, phenyl salicylate, benzyl salicylate, dipropylene glycol salcylate, ethylene glycol salicylate and p-isopropanol phenyl salicylate, cinnamic acid type ultraviolet absorbants such as octyl cinnamate, ethyl-4-isopropyl cinnamate, methyl-2,5-diisopropyl cinnamate, ethyl-2,4-diisopropyl cinnamate, methyl-2,4-diisopropyl cinnamate, propyl p-methoxycinnamate, isopropyl p-methoxycinnamate, isoamyl p-methoxycinnamate, octyl p-methoxycinnamate (2-ethylhexyl p-methoxycinnamate), 2-ethoxyethyl p-methoxycinnamate, cyclohexyl p-methoxycinnamate, ethyl-α-cyano-β-phenyl cinnamate, 2-ethylhexyl-α-cyano-β-phenyl cinnamate and mono-2-ethylhexanoyl di-p-methoxycinnamoylglycerol, benzophenone type ultraviolet absorbants such as 2,4-hydroxybenzophenone, 2,2'-dihydroxy-4-methoxybenzophenone, 2,2'-dihydroxy-4,4'-dimethoxybenzophenone, 2,2',4,4'-tetrahyiroxybenzophenone, 2-hydroxy-4-methoxybenzophenone, 2-hydroxy-4-methoxy-4'-methylbenzophenone, 2-hydroxy-4-benzophenone-5-sulfonate, 4-phenylbenzophenone, 2-hydroxy-4-n-octoxybenzophenone, 2-hydroxy-4-chlorobenzophenone and 2,2'-dihydroxy-4,4'-methoxybenzophenone-3,3'-disulfonate, ultraviolet absorbants such as 3-(4'methylbenzylidene)-d,l-camphor, 3-benzylidene-d,l-camphor, urocanic acid, ethyl urocanate, 2-phenyl-5-methylbenzoxazole, 2-phenyl-5-methylbenzoxazole-5-sulfonic acid, 2-(2'-hydroxy-5-methylphenyl)benzotriazole, 2-(2'-hydroxy-5-t-octylphenyl)benzotriazole, dibenzalzine, dianisoylmethane, 4-methoxy-4'-t-butylbenzoylmethane, 5-(3,3-dimethyl2-norbornylidene)-3-pentan-2-one and guanine, moisture-preserving agents such as polyethylene glycol, polyethylene glycol, dipropylene glycol, glycerol, 1,3-butylene glycol, xylytol, sorbitol, maltitol, mucopolysaccharides and salts thereof [chondroitin sulfuric acid (salt), hyaluronic acid (salt), charonin sulfuric acid, heparin sulfuric acid and keratosulfuric acid], proteoglycans (proteokeratosulfuric acid and proteochondroitin sulfuric acid), (athero)collagen, soluble collagen, cholesteryl-12-hydroxystearate, lactic acid (salt), bile acid (salt), pyrrolidone-carboxylic acid (salt), polyglycerol (EO) PO adduct and glucose EO adduct, organic thickening agents such as gum arabic corageenan, tragacanth gum, carob gum, quince seed (marmello) casein, dextrin, gelatin, sodium pectate, sodium alginase, methyl cellulose, ethyl cellulose, carboxymethyl cellulose hydroxyethyl cellulose, hydroxypropyl cellulose, polyvinyl alcohol, polyvinyl butyral, polyvinyl pyrrolidone, carboxyvinyl polymer, locust bean gum, gua gum, tamarind gum, dialkyldimethyl ammonium sulfate cellulose, xanthane gum, and hyaluronic acid (salt), inorganic thickening agents such as montmorillonite, saponite and hectorite, organically modified mineral thickening agents such as thickening agents obtained by modifying these inorganic thickening agents with quaternary ammonium salt type cationic activators, non-ionic activators, silicone type activators or the like, organic solvents such as acetone, toluene, butyl acetate and ethyl acetate, plasticizers such as acetyltriethyl citrate and acetyltributyl acetate, antioxidants such as butylhydroxytoluene (BHT), butylhydroxyanisole (BHA), tocopherol, catechin, epigallocatechin, epigallocathechin gallate, green tea tannin, propyl gallate, phytic acid and an ester of phosphoric acid with tocopherol and ascorbic acid, antibacterial antiseptic agents such as benzoic acid (salt), salicylic acid (salt), sorbic acid (salt), dehydroacetic acid (salt), alkyl p-hydroxybenzoates (ethyl paraben and butyl paraben) and hexachlorophene, neutral amino acids such as glycine, alanine, valine, leucine, isoleucine, serine, threonine, phenylalanine, tyrosine, tryptophane, cystine, cysteine, methionine, proline, hydroxyproline and DOPA, acidic amino acids and alkali metal salts thereof such as aspartic acid, glutamic acid, asparagine, glutamine and taurine, organic amine salts and basic amino acid salts, basic amino acids and hydrochlorides thereof such as alginine, hystidine and lysine, acylsarcosine salts. (for example, sodium lauroylsarcosine), acylaminoacid salts (for example, sodium lauroylglutamate and sodium acyl β-alanine), glutathione, organic acids such as citric acid, malic acid, tartaric acid and lactic acid, vitamin A and its derivatives, vitamins B such as vitamin $B_6$ hydrochloride, vitamin $B_6$ tripalmitate, vitamin $B_6$ dioctanoate, vitamin $B_2$, derivatives thereof, vitamin $B_{12}$, vitamin $B_{15}$ and derivatives thereof, vitamins C such as ascorbic acid, sulfate ascorbate, an ascorbic acid ester of phosphoric acid and ascorbic acid dipalmitate, vitamins E such as α-tocopherol, β-tocopherol, γ-tocopherol, vitamine E acetate and vitamin E nicotinate, other vitamins such as vitamin H, pantothenic acid and panthetine, various medicines such as nicotinic acid amide, benzyl nicotinate, γ- oyzanole, allantoin, glycyrrhetinic acid and derivative thereof, hinokitiol, musdine, bisabolol, eucalyptol, phytosterol, thymol, inositol, saponins (saikosaponin, carrot saponin and luffa saponin), tannins (gallotannins such as tannic acid and catechins such as catechin, epigallocatechin, epigallocatechin gallate and epicatechin gallate), pantothenyl ethyl ether, ethynylestradiol and placenta extract, natural extracts obtained by extracting licorice, paprika, *Isodon japonicus, Isodon trichocarpus, Inula japonica, Bixa orellana,* sorrel, *Sophora angustifolia, Cinnamonum camphora, Nuphar jaconicum, Houttuynia cordota,* iris, Japanese honeysuckle, celery, geranium, turmeric, dead nettle, tea (green tea and black tea), orange, sage, *Hedera helix, Ruscus,* milfoil, mistletoe, mallow, Cnidium officinale, Japanese green gentian, thyme, clove, *Citrus unshiu, Angelica acutilaba,* pot marigold, orange peel, carrot, onion, wild rose, birch, parsley, gentian, mint fennel, field horsetail, saffron, mustard, soapwort, butcher's broom, grape, ivy, luffa, nettle, pipal, hop, pepper tree, *Cortinellus shiitake,* horse chestnut, *Menyanthes trifoliata, Sapindus mukurossi,* melisse, peach, eucalyptus, parsley, *Rehmannia glutinosa,* lithospermum root, creeping saxifrage arnica, lily, mugwort, beefsteak plant, peony, rosemary, lemon, ginger, rosa fruit, burnet, white birch, raspberry, *Scutellaria baicalenis,* aloe, cucumber, burdock, Cape jasmine, phellodendron, Japanese coptis, gambir-catechu, hydrangea leaves, *Zizyphus jujuba var. inermis, Davallia mariessi, Chamaecyparis pisifera,* Guinea pepper, *Poria cocos,* polypore, *Polyporus umbellatus, brachet fungus,* oyster, *Crptophyta* and *Rhodophyta,* with organic solvents, alcohols, polyhydric alcohols, water and aqueous alcohols, and non-ionic surface active agents, cationic surface active agents, anionic surface active agents, amphoteric surface active agents, perfumes, water, and alcohols.

The hair cosmetic composition according to the present invention has the following advantages.

(a) The diester of phosphoric acid becomes water-soluble or oil-soluble according to the kind of salt, and the diester can be incorporated into any product regardless of the form thereof.

(b) The compound according to the present invention has an excellent stability on the skin and is very safe.

It is considered that the reason why the hair cosmetic composition of the present invention has an effective dandruff-preventing action and a loss of hair-preventing action is that the metabolic reaction of the head skin texture is appropriately adjusted and a formation of a peroxide lipid on the head skin is inhibited.

EXAMPLE

The present invention will now be further illustrated by, but is by no means limited to, the following Examples, wherein all percentages in the composition are expressed on a weight basis unless otherwise noted.

PREPARATION EXAMPLE 1

Preparation of potassium L-ascorbic DL-α-tocopherol phosphate

In 50 ml of benzene was dissolved 6.12 of phosphorus oxytrichloride, and a mixed solution of 8.6 g (0.02 mole) of DL-α-tocopherol and 9.5 g of pyridine in 50 ml of benzene was added dropwise to the above solution while stirring. After termination of the dropwise addition, the mixture was stirred for another 3 hours, the precipitated pyridine hydrochloride was removed by filtration, the filtrate was concentrated under a reduced pressure, and 30 ml of benzene was added to the residual oil.

Separately, 5.2 g (0.024 mole) of 5,6-isopropylideneascorbic acid obtained by acetonation of L-ascorbic acid and 3.2 g of pyridine were dissolved in 120 ml of tetrahydrofuran. The above benzene solution was added dropwise to the tetrahydrofuran solution while stirring, and after termination of the dropwise addition, stirring was conducted for about another 1 hour. The precipitated pyridine hydrochloride was removed by filtration, and the solvent was removed from the filtrate by distillation under a reduced pressure. The obtained oil was dissolved in 30 ml of ethyl alcohol, 150 ml of 1N hydrochloric acid was added to the solution, and the mixture was heated and refluxed for about 20 minutes, cooled, extracted with ethyl acetate, and dried with anhydrous sodium sulfate. Ethyl acetate was removed by distillation, and a crude free acid was obtained as the residue.

This crude free acid was dissolved in about 100 ml of ethyl alcohol, and a solution of potassium hydroxide in ethyl alcohol was gradually dropped into the above solution until the pH value of the solution became neutral, whereby a slightly brownish-white crystal was precipitated. The crystal was recovered by filtration and recrystallized from water ethyl alcohol-acetone to obtain 7.5 g of a white powdery crystal.

Melting point: Carbonization gradually began at about 210° C.

Ultraviolet absorption spectrum (UV): A maximum absorption appeared at about 257 nm.

Silica gel thin layer chromatograph: Rf=0.81 (ethyl alcohol/acetone/water=10/4/1)

Elementary analysis values as $C_{35}H_{55}C_{10}PK_2 \cdot H_2O$: Calculated: C=55.09%, H =7.5%., Found: C=55.32%, H =7.65%

PREPARATION EXAMPLE 2

Preparation of sodium L-ascorbic DL-α-tocopherol phosphate

In 30 ml of water was dissolved 5 g of potassium L-ascorbic DL-α-tocopherol phosphate obtained in Preparation Example 1, and the solution was made acidic by an addition of hydrochloric acid and extracted with ethyl acetate. Ethyl acetate was removed from the extract by distillation to obtain L-ascorbic DL-α-tocopherol phosphate in the form of a free acid (UV absorption spectrum appeared at 285 nm in water). The free acid was dissolved in ethyl alcohol, and a 30% solution of sodium hydroxide was gradually added to the solution until the solution became neutral, whereby a white crystal was obtained. The white crystal was recovered by filtration, washed with ethyl alcohol, and dried to obtain about 4 g of the intended salt.

Elementary analysis values as $C_{35}H_{55}ONa_2 \cdot H_2O$: Calculated: C=57.52%, H =7.86%, Found: C=57.65%, H =7.98%

EXPERIMENTAL EXAMPLE 1

This Example illustrates the dandruff-preventing effect and the loss of hair effect of the compound of the present invention.

To 75 g of ethanol were gradually added 0.2 g of sodium ascorbic α-tocopherol phosphate (Preparation Example 2), 0.2 g of polyoxyethylene (8 moles) oleyl alcohol ether, 24.6 g of purified water, a slight amount of Yellow 1, and a slight amount of a perfume to prepare a hair tonic sample (hereinafter referred to as "phosphoric acid diester-incorporated hair tonic) Similarly, a hair tonic different from the above hair tonic in that the diester of phosphoric acid was not added (water was added instead) was prepared (hereinafter referred to as "diester-free hair tonic ").

Separately, a shampoo comprising 25% of triethanolamine lauroylpolyoxyethylene (3 moles) sulfate (40% aqueous solution), 1% of a carboxyvinyl polymer, 3% of glycerol and 1% of zinc pyrithione (ZPT) and purified water in an amount such that the entire amount was 100% was prepared (hereinafter referred to as "ZPT-incorporated shampoo "). Similarly, a shampoo comprising 1% of sodium ascorbic acid α-tocopherol phosphate instead of ZPT (hereinafter referred to as "phosphoric acid diester-incorporated shampoo ") and a shampoo not containing ZPT or sodium ascorbic acid α-tocopherol phosphate (water was added instead) (hereinafter referred to as "chemical-free shampoo ") were prepared.

Nine men 18 to 55 years old and having scurf on the head were selected as the subjects of the experiment. At the control stage, the hair of all of the men was washed with the chemical-free shampoo and then treated with the diester-free hair tonic, and after two days, the accumulated dandruff was collected. This operation was conducted twice a week for one month (eight times in total). The dandruff was collected by suction from the head skin, using a suction device. The amount of the protein in the collected dandruff was measured by the micro-Kjeldahl method and the average protein amount Pc per operation was determined with respect to each subject. Then, 13 subjects were divided into three groups (5 subjects, 4 subjects and 4 subjects). The hair of the 5 subjects of the first group was washed with the phosphoric acid diester-incorporated shampoo and then treated with the phosphoric acid diester-incorporated hair tonic, and the hair of the 4 subjects of the second group was washed with the ZPT-incorporated shampoo and treated with the phosphoric acid diester-incorporated hair tonic. The hair of the 4 subjects of the third group was washed with the ZPT-incorporated shampoo and then treated with the diester-free hair tonic. The accumulated dandruff was collected from each group after 2 days, and then twice a week for 1 month (8 times in total). The protein quantity in the dandruff collected during this period (experimental period) was measured in the same manner for in the control, and the average protein amount Ps per operation was determined with respect to each subject.

The dandruff reduction ratio (%) during the experimental period was calculated according to the formula $(Pc - Ps)/Ps \times 100$. The results are shown in Table 1.

venting effect compared to the shampoo in which known ZPT is incorporated as the dandruff-preventing agent. It is also obvious that the sodium ascorbic acid tocopherol phosphate-incorporated hair tonic has a remarkable dandruff-preventing effect, compared with the diester-free hair tonic.

EXPERIMENTAL EXAMPLE 2

The loss of hair-preventing effect was examined by changing the amount of the potassium ascorbic acid α-tocopherol phosphate incorporated in the hair tonic, and six kinds of hair tonics having a composition shown in Table 2 were prepared. Thirty men 25 to 55 years old were selected at random as the subjects, and 5 subjects were alloted to each sample hair tonic. The hair tonic was used once a day, and the number of hairs lost over 2 days after washing, during the control period (the above-mentioned phosphoric acid diester-free hair tonic was used), was compared with the number of hairs lost for 2 days after washing during the experimental period. When the reduction ratio of the loss of hair was higher than 10%, it was judged that a loss of hair-preventing effect was obtained, and when the ratio of the fallen hairs was lower than 10%, it was judged that the loss of hair-preventing effect was not obtained. The results are shown in Table 2.

TABLE 2

| | Sample No | | | | | |
|---|---|---|---|---|---|---|
| | 1 | 2 | 3 | 4 | 5 | 6 |
| Composition of Hair Tonic | | | | | | |
| phosphoric acid diester (%) obtained in Example 2 | 0.001 | 0.01 | 0.05 | 0.1 | 2 | 10 |
| ethanol (%) | ← 75% → | | | | | |
| purified water | in amount such that total quantity was 100% | | | | | |
| Dandruff-Preventing Effect | | | | | | |
| effective (number of subjects) | 1 | 3 | 4 | 5 | 5 | 5 |
| not effective (number of subjects) | 4 | 2 | 1 | 0 | 0 | 0 |

In the case of the hair tonic comprising 0.001% by weight of the phosphoric acid diester of the present invention (sample No. 1), the loss of hair-preventing effect was observed in one subject among five subjects. In the case of sample No. 2 where the amount of the phosphoric acid diester was increased 10 times, a remarkable effect was observed in 3 subjects among 5 subjects. A remarkable loss of hair effect was observed

TABLE 1

| First Group (phosphoric acid diester-incorporated shampoo and hair tonic) | | Second Group (ZPT-incorporated shampoo and phosphoric acid diester-incorporated hair tonic) | | Third Group (ZPT-incorporated shampoo and diester-free hair tonic) | |
|---|---|---|---|---|---|
| Subject No. | Dandruff control ratio (%) | Subject No. | Dandruff control ratio (%) | Subject No. | Dandruff control ratio (%) |
| 1 | 34.71 | 1 | 29.01 | 1 | 21.19 |
| 2 | 39.81 | 2 | 28.16 | 2 | 26.01 |
| 3 | 41.32 | 3 | 29.91 | 3 | 20.91 |
| 4 | 37.92 | 4 | 19.81 | 4 | 18.22 |
| 5 | 37.11 | — | — | — | — |
| average | 38.17 | average | 26.72 | average | 21.58 |

From the shown in Table 1 results, it can be seen that the sodium ascorbic acid α-tocopherol phosphate-incorporated shampoo has an excellent dandruff-preventing effect compared to the shampoo in which known ZPT is incorporated as the dandruff-preventing agent. It is also obvious that the sodium ascorbic acid tocopherol phosphate-incorporated hair tonic has a remarkable dandruff-preventing effect, compared with the diester-free hair tonic.

in all 5 subjects when the potassium ascorbic acid tocopherol was incorporated in an amount of at least 0.1% by weight (sample No. 4).

EXPERIMENTAL EXAMPLE 3

The anti-oxidizing action of the diester of phosphoric acid with ascorbic acid and tocopherol according to the present invention will now be described.

A screw tube having a capacity of 50 ml was charged with 1 g of ethyl linoleate, and 0.2 mg of a sample substance shown in Table 3 was added and mixed with the ethyl linoleate. The mixture was then irradiated with ultraviolet rays for 3 hours to effect air oxidation, and the amount of the ethyl linoleate peroxide formed was measured by high-speed liquid chromatography (HPLC). The amount of the peroxide shown in Table 3 is a relative value calculated on the assumption that the value obtained when the sample substance was not added (control) was 100%.

TABLE 3

| Sample Substance | Amount (%) of Lipid Peroxide |
|---|---|
| Control | 100 |
| α-tocopherol/vitamin A acid ester | 71.9 |
| vitamin E/nicotinic acid ester | 72.5 |
| tocopherol | 72.7 |
| potassium ascorbic acid α-tocopherol phosphate | 51.2 |

According to the results of research by the present inventors, it was found that a very close relationship is established between a formation of dandruff and the amount of lipid peroxide in dandruff. Namely, it was found that if the amount of the lipid peroxide in the head skin is reduced, the formation of dandruff can be controlled, and accordingly, an antioxidant capable of reducing the quantity of a lipid peroxide is inherently effective as a dandruff-control agent.

As apparent from the results shown in Table 3, the compound of the present invention has a much higher antioxidizing function than the conventional tocopherol esters.

EXAMPLE 1

To 60 g of ethyl alcohol, 2 g of polyoxyethylene (40 moles) oleyl alcohol and an appropriate amount of a perfume were added, and a solution was formed at room temperature to obtain an alcohol phase. Separately, 5 g of glycerol and 0.1 g of potassium ascorbic acid α-tocopherol phosphate were added to 32.9 g of purified water, and the mixture was heated to form a solution, the solution was cooled, and an appropriate amount of Yellow 1 was added to the solution. The alcohol phase was then added to the aqueous phase to effect solubilization and obtain a hair tonic having a dandruff-preventing effect and a loss of hair-preventing effect.

EXAMPLE 2

To 50.0 g of ethyl alcohol, 20 g of polyoxypropylene butyl ether and an appropriate amount of a perfume were added and a solution was formed at room temperature. Then, 0.2 g of magnesium ascorbic acid μ-tocopherol phosphate was added to 29.8 g of purified water and the mixture was heated to form a solution. After cooling, an appropriate amount of Blue 2 was added to the solution, and this solution was mixed with the above-mentioned alcohol phase to obtain a hair liquid having a dandruff-preventing effect and a loss of hair-preventing effect.

EXAMPLE 3

An oil phase was prepared by heating at 80° C a mixture comprising 2 g of stearic acid, 1.5 g of cetyl alcohol, 3 g of vaseline, 13 g of liquid paraffin, 1 g of polyoxyethylene (10 moles) mono-oleate, and an appropriate amount of a perfume. Separately, an aqueous phase was prepared by heating at 80° C a mixture comprising 5 g of propylene glycol, 1 g of triethanolamine, 0.05 g of sodium ascorbic acid β-tocopherol phosphate, and 73.45 g of purified water. The oil phase was gradually added to this aqueous phase while stirring, to effect emulsification, and the emulsion was cooled to obtain a head skin milky lotion having a dandruff-preventing effect and a loss of hair-preventing effect.

EXAMPLE 4

An oil phase was prepared by heating at 80° C a mixture comprising 2 g of stearic acid, 7 g of stearyl alcohol, 2 g of lanoline, 5 g of squalane, 6 g of octyl dodecanol, 3 g of polyoxyethylene (10 moles) cetyl ether, 2 g of glyceryl monostearate, and an appropriate amount of a perfume. Separately, an aqueous phase was prepared by heating at 80° C a mixture comprising 5 g of propylene glycol, 2 g of sodium ascorbic acid β-tocopherol phosphate, and 66.0 g of purified water. The oil phase was gradually added to the aqueous phase while stirring, to effect emulsification, and the emulsion was cooled to obtain a hair cream having a dandruff-preventing effect and a loss of hair preventing effect.

EXAMPLE 5

To 70.0 g of purified water were added 15 g of triethanolamine lauryl sulfate, 5 g of coconut oil fatty acid monoethanolamide, 10.0 g of calcium ascorbic acid γ-tocopherol phosphate, and appropriate amounts of Red 2, Red 22 and a perfume, and the mixture was heated and was then cooled to obtain a hair shampoo having a dandruff-preventing effect and a loss of hair-preventing effect.

EXAMPLE 6

In 74.99 g of purified water 3.5 g of polyethylene glycol 1500, 1 g of triethanolamine and 0.01 g of potassium ascorbic acid δ-tocopherol phosphate were dissolved under heating, and the solution was maintained at 70° C. Then, 2.5 g of stearic acid, 1.5 g of cetyl alcohol, 5 g of vaseline, 10 g of squalane, and 2 g of polyoxyethylene (10 moles) mono-oleate were heated, dissolved, maintained at 70° C. and added to the above-mentioned aqueous phase. After preliminary emulsification, the mixture was uniformly emulsified by a homomixer and gradually cooled to obtain a hair lotion having a dandruff-preventing effect and a loss of hair-preventing effect.

We claim:

1. A method of treating a patient having dandruff, which comprises administering an anti-dandruff effective amount of a hair cosmetic composition comprising (i), as an active component, 0.1% to 10% by weight of at least one component selected from the group consisting of diesters of phosphoric acids with ascorbic acid and tocopherol, having the formula (I), and salts thereof:

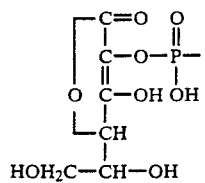
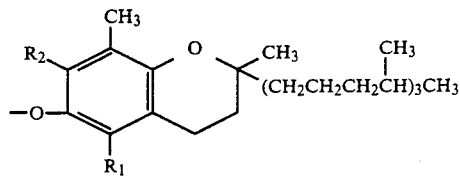

wherein R₁ represents H or CH₃ and R₂ represents H or CH₃; and (ii) a carrier.

2. A method of treating a patient suffering from hair loss due to dandruff, which comprises administering an anti-dandruff effective amount of a hair cosmetic composition comprising (i), as an active component 0.1% to 10% by weight of at least one component selected from the group consisting of diesters of phosphoric acids with ascorbic acid and tocopherol, having the formula (I), and salts thereof:

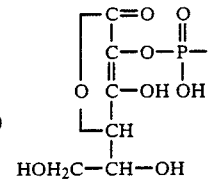
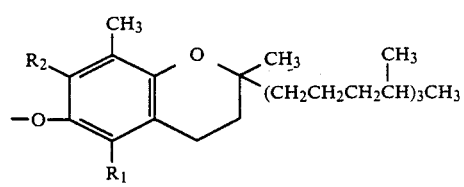

wherein R₁ represents H or CH₃ and R₂ represents H or CH₃; and (ii) a carrier.

* * * * *